United States Patent [19]

Ruland et al.

[11] Patent Number: 4,550,173

[45] Date of Patent: Oct. 29, 1985

[54] DITRIAZOLYLVINYL PHENYL KETONES

[75] Inventors: Alfred Ruland, Hirschberg; Wolfgang Reuther, Heidelberg; Ernst-Heinrich Pommer, Limburgerhof; Eberhard Ammermann, Ludwigshafen, all of Fed. Rep. of Germany

[73] Assignee: BASF Aktiengesellschaft, Fed. Rep. of Germany

[21] Appl. No.: 571,454

[22] Filed: Jan. 17, 1984

[30] Foreign Application Priority Data

Jan. 22, 1983 [DE] Fed. Rep. of Germany ....... 3302098

[51] Int. Cl.$^4$ .................. A01N 43/64; C07D 249/08
[52] U.S. Cl. ........................................ 548/262; 71/27; 71/902; 260/465 G; 568/325; 568/335; 568/337
[58] Field of Search .......................................... 548/262

[56] References Cited

U.S. PATENT DOCUMENTS

| | | | |
|---|---|---|---|
| 4,235,620 | 11/1980 | Lewis et al. | 548/262 |
| 4,291,044 | 9/1981 | Jages et al. | 548/262 |
| 4,379,921 | 4/1983 | Funaki et al. | 548/262 |

FOREIGN PATENT DOCUMENTS 1592516  7/1981  United Kingdom .

OTHER PUBLICATIONS

Kashima et al., J. Heterocyclic Chemistry, vol. 21, pp. 133–137 (1984).
Hoffmann et al., Chem. Abstracts, vol. 81, Abstract No. 77840d (1974). QD1A51.
Landw. Forschung: Special Issue 27 (1972), 74–82.

*Primary Examiner*—Alton D. Rollins
*Attorney, Agent, or Firm*—Keil & Weinkauf

[57] ABSTRACT

Ditriazolylvinyl phenyl ketones of the formula I

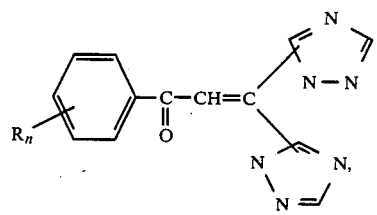

where R is halogen, alkyl of 1 to 6 carbon atoms, alkoxy of 1 to 6 carbon atoms, trifluoromethyl, cyano, nitro, phenyl or phenoxy, and n is an integer from 0 to 5, and the two triazole rings can, as desired, be bonded in the 1-position or 4-position to the vinyl group, their preparation and their use as nitrification inhibitors.

5 Claims, No Drawings

DITRIAZOLYLVINYL PHENYL KETONES

The present invention relates to novel ditriazolylvinyl phenyl ketones, their preparation and a method of inhibiting nitrification.

Ammonium nitrogen in the soil is oxidized by bacteria of the nitrosomonas and nitrobacter strains to nitrate nitrogen via nitrite nitrogen. The extent of nitrification depends on the type, pH, moisture content and biological activity of the soil. In contrast to ammonium nitrogen, nitrate nitrogen tends to be washed out, especially from lighter soils, so that it is no longer available for plant nutrition, and there is a danger that the nitrate concentration in the ground water will increase; hence, inhibition of nitrification is particularly important.

A commerical product used, inter alia, for this purpose, is Dazomet (3,5-dimethyltetrahydro-1,3,5-thiadiazine-2-thione). A literature reference for Dazomet, 1,3-dichloropropene, 1,2-dibromo-3-chloropropane and 2-chloro-6-trichloromethylpyridine is Down to Earth 32 (1976), 14–17. The last-mentioned compound (common name, nitrapyrin) is sold as a nitrification inhibitor under the trade name (R)N-Serve. Another commerical product is dicyanodiamide, which has become an important nitrification inhibitor (Landw. Forschung: Special issue 27 (1972), 74–82). Finally, pyrimidine derivatives and pyrazole derivatives may be mentioned (cf. for example German Laid-Open Application DOS 2,745,833). However, these substances do not satisfy all requirements in respect of their efficiency, duration of action, cost-efficiency or harmlessness or their performance characteristics, such as water-solubility, dispersibility, vapor pressure, etc.

It is an object of the present invention to provide improved nitrification inhibitors which are superior to the conventional ones in a very large number of the stated properties.

We have found that this object is achieved, and that ditriazolylvinyl phenyl ketones of the formula I

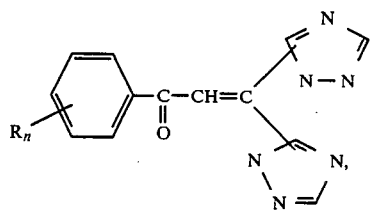

I where R is fluorine, bromine, iodine or preferably chlorine, or alkyl of 1 to 6 carbon atoms, preferably methyl, alkoxy of 1 to 6 carbon atoms, trifluoromethyl, cyano, nitro, phenyl or phenoxy, and n is an integer from 0 to 5, preferably 0, 1 or 2, and the two triazole rings are bonded in the 4-position or, preferably, in the 1-position to the vinyl group, have surprisingly good properties as nitrification inhibitors.

Furthermore, we have found that the compounds of the formula I are obtained very readily and in good yields by reacting a dihalovinyl ketone of the formula II, where R and n have the above meanings and X is fluorine, iodine or, preferably, chlorine or bromine, with 1,2,4-triazole.

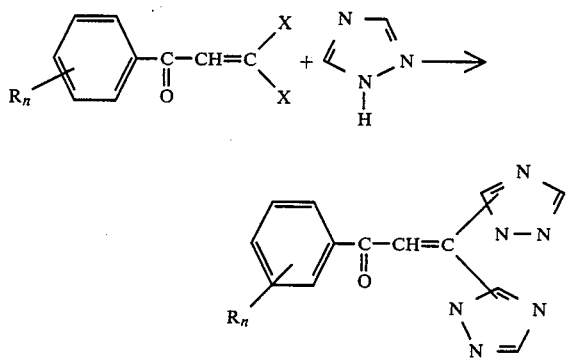

The reaction is carried out in the presence of a solvent, e.g. dimethylformamide, dimethyl sulfoxide, hexamethylphosphoric triamide, tetrahydrofuran, dioxane or acetonitrile, and of a basic substance, e.g. an alkali metal or alkaline earth metal hydroxide, carbonate, alcoholate or phenolate, preferably sodium carbonate or potassium carbonate.

The dihalovinyl ketones required for the reaction are known, and can be prepared by a conventional method (cf. for example Houben-Weyl-Müller, Methoden der organischen Chemie, 4th Edition, Georg Thieme Verlag, Stuttgart 1968, Vol. 7/4, page 442).

The substances according to the invention can be employed alone or as a mixture with solid or liquid fertilizers which contain ammonium nitrogen, urea or ammonia; they may lso be applied together with plant-treatment agents or soil conditioners. Advantageously, the active ingredients are applied simultaneously with the fertilizer. The amounts used are from 0.05 to 10, preferably from 0.5 to 3, kg/ha. When used in combination with solid or liquid fertilizers, the active ingredients can be employed in amounts of from 0.5 to 10 percent by weight, based on fertilizer nitrogen.

The novel nitrification inhibitors are very effective, non-toxic, non-volatile, sufficiently water-soluble and stable. They remain in the soil for a long time, and are therefore effective over a long period. Hence, not only are they useful in terms of environmental protection, in that they prevent nitrate from being washed into the ground water, but they also substantially improve the utilization of the fertilizer nitrogen, particularly in lighter soils.

In the Examples which follows, parts are by weight. Parts by volume bear the same relation to parts by weight as that of the liter to the kilogram.

EXAMPLE 1

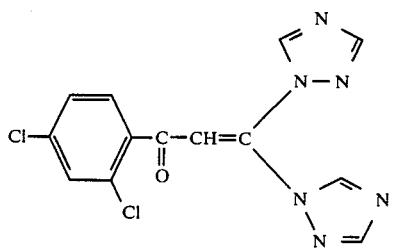

1,1-Bis(1,2,4-triazolyl)-3-(2,4-dichlorophenyl)-propen-3-one 27.1 parts of 1,1-dichloro-3-(2,4-dichlorophenyl)-propen-3-one, 13.8 parts of 1,2,4-triazole and 13.8 parts of potassium carbonate in 300 parts by volume of acetonitrile were refluxed for 2 hours, after which the mixture was cooled to room temperature, 300 parts by volume of water were added, the mixture was extracted with twice 500 parts by volume of methylene chloride, and the extracts were dried over sodium sulfate and evaporated to dryness under reduced pressure.

Yield: 27.8 parts (80% of theory)
Mp.: 200°–203° C.
$C_{13}H_8Cl_2N_6O$: Calculated; C 46.6, H 2.7, N 25.1, Cl 21.2; (335) Found; C 46.8, H 2.5, N 24.7, Cl 20.9.

The products below were obtained similarly to Example 1:

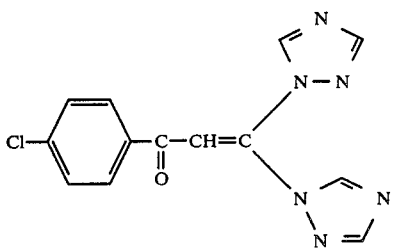

2.

1,1-Bis(1,2,4-triazolyl)-3-(4-chlorophenyl)-propen-3-one Mp.: 202°–203° C.
$C_{13}H_9ClN_6O$: Calculated; C 51.9, H 3.0, N 28.0, Cl 11.8; (300.5) Found; C 52.1, H 3.0, N 27.9, Cl 11.8.

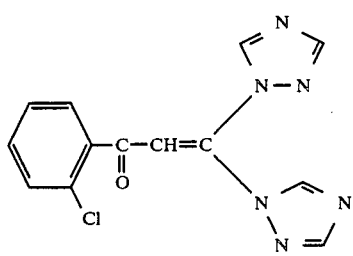

3.

1,1-Bis(1,2,4-triazolyl)-3-(2-chlorophenyl)-propen-3-one Mp.: 168° C.
$C_{13}H_9ClN_6O$: Calculated; C 51.9, H 3.0, N 28.0, Cl 11.8; (300.5) Found; C 51.9, H 3.0, N 27.7, Cl 11.6.

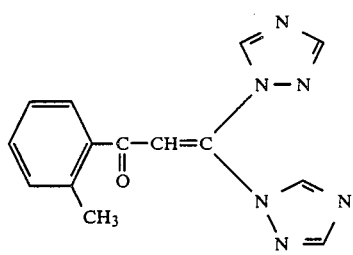

4.

1,1-Bis(1,2,4-triazolyl)-3-(2-methylphenyl)-propen-3-one Mp.: 167° C.
$C_{14}H_{12}N_6O$: Calculated; C 60.0, H 4.3, N 30.0; (280) Found; C 60.0, H 4.2, N 29.2.

Application 220 mg of ammonium sulfate were mixed thoroughly with 200 g of a loamy, sandy soil whose moisture content had been brought to 50% of the maximum water capacity. The active ingredients, dissolved in 0.2 ml of acetone, were then added in amounts of 1 ppm, based on moist soil. The soil samples were carefully mixed and the acetone was evaporated, after which the samples were incubated for 28 days at 21° C. together with the controls without the addition of the active ingredient, incubation being carried out in 1-liter glass vessels covered with aluminum foil to avoid water loss. Thereafter, 2.5 g portions of the soil samples were introduced into 100 ml conical flasks, and 22.5 ml of a 0.1N potassium sulfate solution were added. The mixture was shaken for 30 minutes, after which it was filtered, and 2.5 ml portions of the soil extracts were mixed with 16.25 ml of distilled water. To detect ammonium ions still present in the soil extract, 1.25 ml of Nessler reagent were then added, the mixture being shaken thoroughly. The color changes were then measured photometrically at a wavelength of 420 nm. The amounts of ammonium sulfate still present in the soil samples were determined by comparison with standard curves obtained by measurements on solutions containing known amounts of ammonium sulfate. The percentage inhibition of nitrification in the treated soil samples in comparison with the untreated soil samples (only ammonium sulfate added) was calculated in accordance with the following formula:

% inhibition of nitrification = $(a-b)/a \cdot 100$ a = nitrification rate for ammonium sulfate
b = nitrification rate for ammonium sulfate + nitrification inhibitor.

TABLE

| Active ingredient example | % inhibition of nitrification four weeks after the addition of 1 ppm of active ingredient to the soil |
| --- | --- |
| 1 | 79 |
| 2 | 94 |
| 3 | 98 |
| 4 | 98 |
| Comparative experiment: 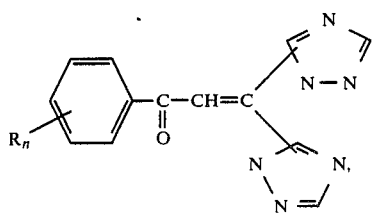 71 | |

(No. 95 from German Laid-Open Application DOS 2,745,833).

We claim:
1. A ditriazolylvinyl phenyl ketone of the formula I where R is halogen, alkyl of 1 to 6 carbon atoms, alkoxy of 1 to 6 carbon atoms, trifluoromethyl, cyano, nitro, phenyl or phenoxy, and n is an integer from 0 to 5, and the two triazole rings are bonded in the 1-position or 4-position to the vinyl group.

2. A ditriazolylvinyl phenyl ketone of the formula I of claim 1 where R is chlorine or methyl and n is 0, 1 or 2, and the two triazole rings are bonded in the 1-position to the vinyl group.

3. A compound of the formula I of claim 1, wherein R is chlorine and n is 2.

4. A compound of the formula I of claim 1, wherein R is chlorine and n is 1.

5. A compound of the formula I of claim 1, wherein R is methyl and n is 1.

* * * * *